(12) United States Patent
Berkelaar (10) Patent No.: US 9,675,329 B2
(45) Date of Patent: Jun. 13, 2017

(54) ENDOSCOPIC SURGICAL INSTRUMENT

(71) Applicant: Gerry Berkelaar, Norwell, MA (US)

(72) Inventor: Gerry Berkelaar, Norwell, MA (US)

(73) Assignee: Multi Scopic Instruments, LLC, Norwell, MA (US)

( * ) Notice: Subject to any disclaimer, the term of this patent is extended or adjusted under 35 U.S.C. 154(b) by 627 days.

(21) Appl. No.: 14/057,714

(22) Filed: Oct. 18, 2013

(65) Prior Publication Data

US 2014/0058363 A1 Feb. 27, 2014

Related U.S. Application Data

(63) Continuation-in-part of application No. 12/804,651, filed on Jul. 27, 2010, now abandoned.

(60) Provisional application No. 61/271,765, filed on Jul. 27, 2009.

(51) Int. Cl.

| A61B 17/00 | (2006.01) |
|---|---|
| A61B 1/00 | (2006.01) |
| A61B 1/005 | (2006.01) |
| A61B 34/00 | (2016.01) |
| A61B 34/30 | (2016.01) |

(52) U.S. Cl.
CPC ...... *A61B 17/00234* (2013.01); *A61B 1/0052* (2013.01); *A61B 1/00105* (2013.01); *A61B 34/70* (2016.02); *A61B 1/0057* (2013.01); *A61B 2017/0046* (2013.01); *A61B 2034/306* (2016.02)

(58) Field of Classification Search
CPC ............ A61B 17/062; A61B 17/00234; A61B 17/0218; A61B 1/0052; A61B 1/32
USPC ...................... 606/1, 205; 600/148, 201, 204
See application file for complete search history.

(56) References Cited

U.S. PATENT DOCUMENTS

| 5,395,369 | A |   | 3/1995 | McBrayer et al. |
|---|---|---|---|---|
| 5,454,827 | A |   | 10/1995 | Aust et al. |
| 5,490,819 | A | * | 2/1996 | Nicholas ................. A61B 1/32 600/201 |
| 5,578,052 | A |   | 11/1996 | Koros et al. |
| 5,762,067 | A | * | 6/1998 | Dunham .............. A61B 1/0052 600/148 |
| 5,782,749 | A | * | 7/1998 | Riza .................... A61B 17/2909 600/117 |
| 5,846,240 | A | * | 12/1998 | Kortenbach .......... A61B 18/14 606/174 |

(Continued)

*Primary Examiner* — William Thomson
*Assistant Examiner* — Victor Shapiro
(74) *Attorney, Agent, or Firm* — Sunstein Kann Murphy & Timbers LLP (57) ABSTRACT

An articulating surgical instrument includes a case having a trigger handle, a sheath coupled to the case, a flexible bending section coupled to the sheath, an end effector removably attachable to the bending section, a set of cables that control position of the bending section, at least two motors coupled to the cables, and a user control module configured to control position of the bending section and the end effector. The instrument further includes a pushrod disposed within the sheath and within the bending section that is configured for axial motion relative to the sheath and the bending section and rotational motion within the sheath and the bending section. The pushrod is coupled to the trigger handle and removably coupled to the end effector, so that rotational motion of the pushrod effectuates rotation of the end effector and axial motion of the pushrod is controllable by the trigger handle.

8 Claims, 7 Drawing Sheets

(56) References Cited

U.S. PATENT DOCUMENTS

| | | | |
|---|---|---|---|
| 5,860,995 A | 1/1999 | Berkelaar | |
| 6,506,208 B2 * | 1/2003 | Hunt | A61B 17/29 606/205 |
| 7,322,935 B2 * | 1/2008 | Palmer | A61B 17/0218 600/204 |
| 7,678,117 B2 * | 3/2010 | Hinman | A61B 1/0055 606/1 |
| 2005/0090809 A1 * | 4/2005 | Cooper | A61B 17/00234 606/1 |
| 2006/0020287 A1 * | 1/2006 | Lee | A61B 17/062 606/205 |

* cited by examiner

ENDOSCOPIC SURGICAL INSTRUMENT

This application is a continuation in part of application Ser. No. 12/804,651, filed on Jul. 27, 2010, which in turn claims from the benefit of Provisional Application Ser. No. 61/271,765 filed Jul. 27, 2009. Each of these related applications is hereby incorporated herein by reference in its entirety.

TECHNICAL FIELD

The present invention relates to surgical apparatus, and more particularly to instruments for performing laparoscopic, endoscopic, and natural orifice translumenal endoscopic surgery.

BACKGROUND ART

Devices of the type to which embodiments of the invention are directed are well known in the prior art. Generally classed as laparoscopic or endoscopic surgical instruments, their purpose is to perform surgical procedures within the body through relatively small incisions which allow the insertion of small surgical tools with effectors mounted on elongated shafts which are manipulated or articulated to position the surgical tool and then are further operated to achieve the desired surgical procedure. The articulation, positioning, and activation of the tools are all controlled by a corresponding handpiece located outside the body.

Illumination and viewing of the internal surgical site is accomplished by, for example, an additional device of the same general type employing a light source and miniature-imaging device such as a video camera.

Examples of prior art instruments are shown in U.S. Pat. No. 5,454,827, to Aust et al., for a distal tip articulation mechanism; U.S. Pat. No. 5,578,052, to Koros et al., for a separable handpiece and articulation section; and U.S. Pat. No. 5,860,995, to Berkelaar, for an end effecter articulation assembly

SUMMARY OF EMBODIMENTS

In contrast to the prior art, embodiments of the present invention provide improved devices and assemblies for operating an end effecter, rotating the end effecter about the longitudinal axis of the articulation portion of the instrument, as well as for a control and operation system for articulating or bending the tip of the articulation portion and an attached end effecter.

The handpiece and articulation sections may also be separable in order to prolong the life of one or the other components of the instrument, to use multiple articulation sections with different end effecters with a single handpiece, and to provide for the prevention of reuse of a particular articulation portion or section.

In one embodiment, the invention provides an articulating surgical instrument for endoscopic surgical procedures. The instrument of this embodiment includes a case having a handpiece portion incorporating therein a trigger handle; a sheath (called a "shaft" in my application Ser. No. 12/804,651), having a set of passageways therein, with a proximal end coupled to the case; a flexible bending section having a proximal end coupled to a distal end of the sheath; and an end effector removably attachable to a distal end of the bending section. Additionally, the embodiment includes a set of cables, coupled to the flexible bending section and disposed in the sheath, that control position of the distal end of the bending section; a set of at least two motors, disposed in the case, coupled to the set of cables, so as to control the position of the distal end of the bending section; a user control module, coupled to the set of motors, configured to control the position of the bending section and therefore of the end effector; and a pushrod disposed within the sheath and within the bending section. The pushrod is configured for both (i) axial motion relative to the sheath and the bending section and (ii) rotational motion within the sheath and the bending section, the pushrod having a proximal end coupled to the trigger handle and a distal end removably coupled to the end effector, so that rotational motion of the pushrod effectuates rotation of the end effector and axial motion of the pushrod is controllable by the trigger handle.

In a further related embodiment, the case is configured to be removably attachable to an assembly that includes the sheath, the bending section, and the end effector. Optionally, each of the cables is removably coupled to a corresponding connector pin in the case, and the connector pins in the case are coupled to the set of motors. In a further related embodiment, (a) each of the cables is removably coupled via a connector clip to a corresponding connector pin in the case; (b) each connector clip is configured to be deformed upon removal of the assembly from the case; (c) deformation of such connector clip prevents its operable recoupling to the connector pin, so that the assembly cannot be reattached to the case in a manner enabling reuse of the assembly after it has been removed from the case.

Figure 1:
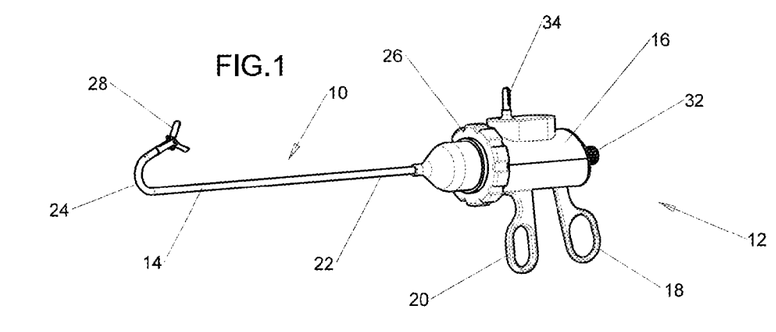
FIG. 1 is a perspective frontal (distal) view of the preferred embodiment of the invention.

More specifically, the embodiment 10 of FIG. 1 may be summarized as an endoscopic surgical instrument composed of an operational handpiece, a reposable (meaning reusable multiple times, then discarded) elongated flexible or rigid section having a flexible bending or pivot portion. These two components may be permanently connected, or separate and connectable. Additionally a single-use disposable end effector can be connected to the distal end of the reposable section. The mechanism joining the components may optionally include an arrangement for preventing reuse of the reposable section or the end effector by, for example, destroying or altering a portion of the connecting linkage to preclude the possibility of reconnection.

The disposable end effector can be mounted on the distal end of the bending section. Additionally the disposable end effector can be mounted on the distal end of the flexible reposable or rigid reposable section without the use of a bending section. In this last instance, the articulation is achieved by means of a pivoting motion controlled by cables.

In this embodiment, there are four cables which control the orientation of the end effector. The end effector can be attached to a bending section and a pushrod provides the capability of opening and closing the end effector. In various embodiments, the end effector is implemented to pivot only, bend only, or both bend and pivot.

The handpiece contains the control mechanisms for positioning and operating a surgical tool or end effector disposed at the tip of the articulation section. These controls may include a knob or lever for rotating a flexible link or rod connected to the end effecter for rotating the end effecter, means to laterally move the same or an additional link to activate the end effector, such as a scissors, and hand or motor operated means to simultaneously pull and release appropriate cable or wire connections to the bending portion to alter or articulate its position or orientation to any point within a spherical space along the longitudinal axis of the instrument.

Electronic controls for achieving the articulation of the bending portion through the use of motor driven gear assemblies are also disclosed.

The reposable section, in general, is an elongated rigid or flexible hollow sheath with a flexible bending portion, containing the above mentioned cables, links, and/or rods. The shaft, providing the main support structure for the end effecter, may be comprised in part of a series of segments or links which will move in relation to one another to produce the articulation in the bending section. In one implementation the segments may be implemented by hollow universal joints.

These and other features and advantages of the invention will be more fully understood from the following description of the preferred embodiment in conjunction with the accompanying drawings.

DETAILED DESCRIPTION OF THE SPECIFIC EMBODIMENTS

FIG. 1 is a perspective frontal view of the preferred embodiment of the laparoscopic instrument of the invention for performing multiscopic surgery that is capable of holding, grasping, cutting, hooking, manipulating, burning, and coagulating tissue along a non-linear trajectory. This instrument is a combination of an operational handpiece FIG. 3 and a reposable section FIG. 4. A variety of different articulation sections and their associated end effectors are used to perform different surgical tasks.

As shown, handpiece 12 has an outer case 16 surrounding and supporting control mechanisms to be described in detail below, a trigger handle 18, and an opposing finger grip 20. Reposable section 14 includes an elongated hollow sheath 22, a flexible bending section 24, and joining nut 26 for attaching handpiece 12 and reposable section 14. An end effecter or surgical tool 28 is attached or mounted on bending section 24.

Figure 4:
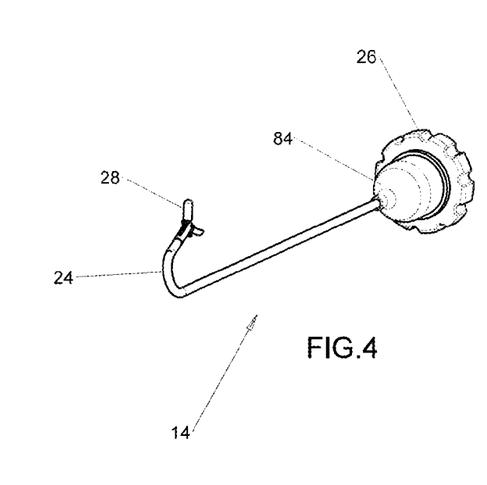
FIG. 4 is a perspective frontal view of a separated reposable (reposable is defined as being able to use the part several times before disposing of it). Reusable components, such as the handpiece, may be reused until a new generation of the instrument is available or the instrument fails and can no longer function.
Figure 5:
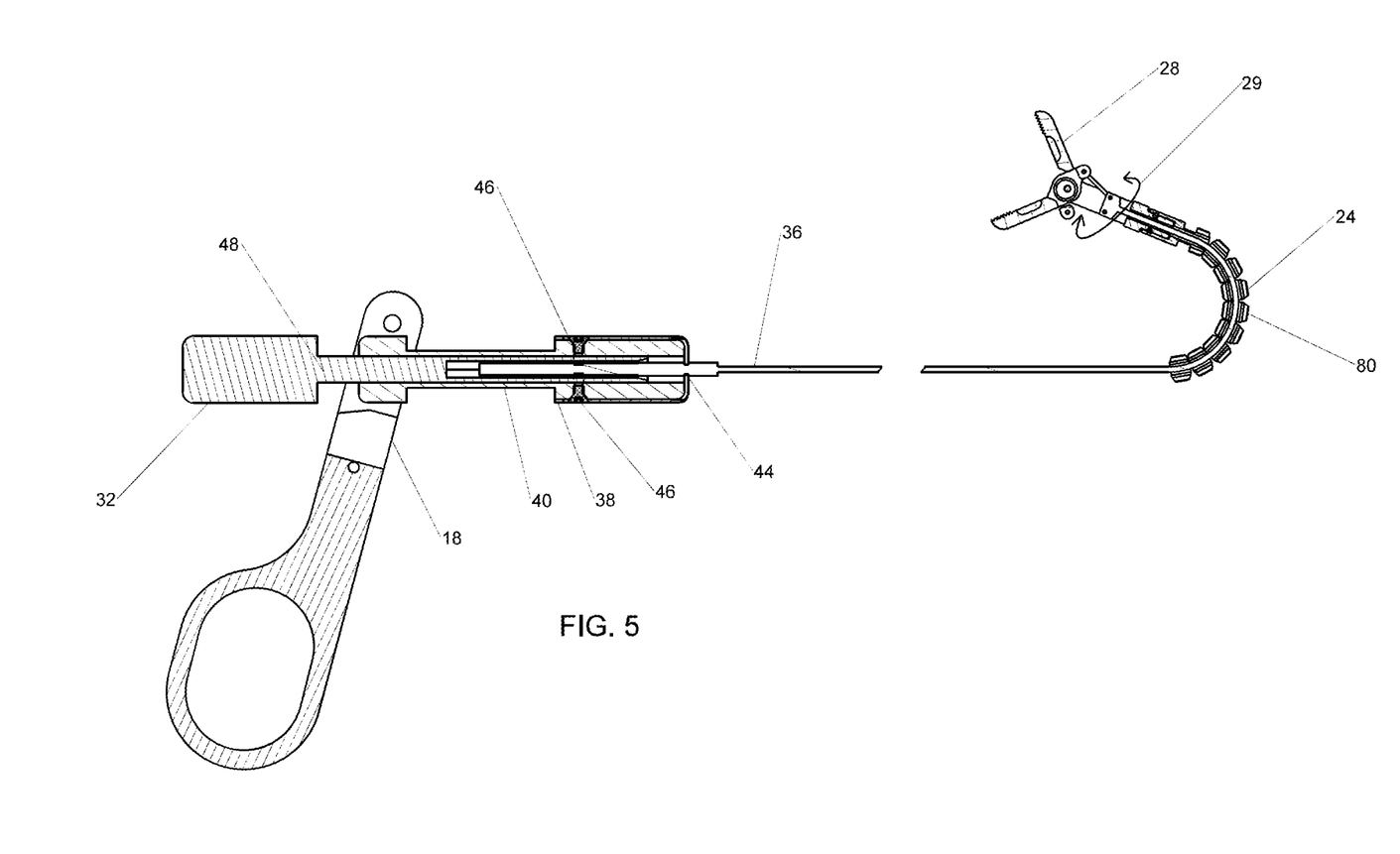
FIG. 5 is a partial cross-sectional view of a portion of FIG. 2 along line A-A.

As shown in FIGS. 1, 2, 4, and 5, the flexible bending section 24 is implemented by a series of connected segments, coupled in a manner to permit flexing at each segment. Other implementations of the flexible bending section 24 are within the scope of the present invention. For example, there may be employed a series of universal joints that are cannulated to accept the flexible pushrod 36 (FIG. 5).

Figure 2:
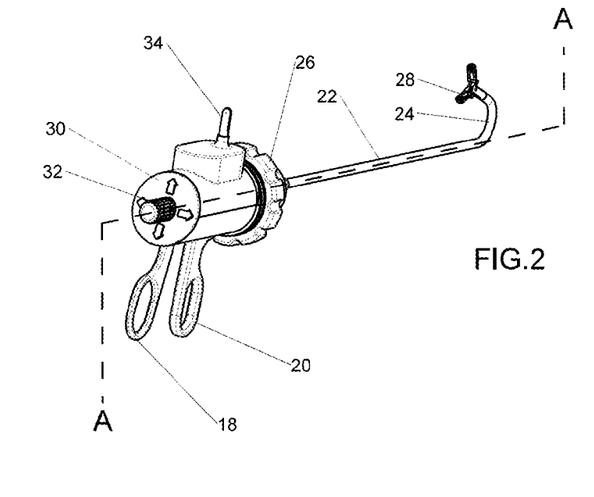
FIG. 2 is an isometric view of the instrument assembled.

FIG. 2 is a rearward or proximal view of the instrument of FIG. 1, further showing a four quadrant control mechanism 30 mounted on case 16 for controlling the position or orientation of bending section 24. A rotary thumb actuator or a set of pushbuttons 32 for rotating the end effector 28 is also mounted on case 16 in conjunction with four quadrant control 30. An electrical connection post 34 for enabling cauterization procedures is further positioned atop case 16.

Figure 3:
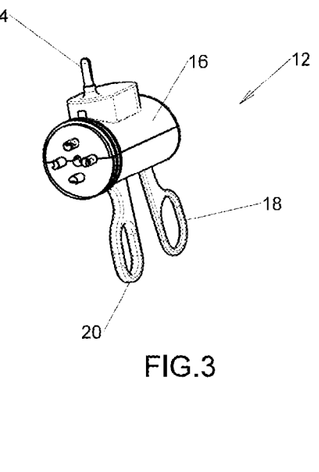
FIG. 3 is a perspective frontal view of a separated portion of the embodiment of FIG. 1.

FIGS. 3 and 4 illustrate handpiece 12 and reposable section 14 separated from one another. It can be seen that the nut 26 of FIG. 4 is used to removably engage the reposable section 14 with the handpiece 12. FIGS. 1-4 above present an overview of the general configuration of an embodiment of the invention, the components and operation of which will now be described in accordance with FIGS. 5-18 in more particular detail as follows.

FIG. 5 shows, in cross-sectional format, the components and control assembly which provide the mechanical embodiment of the axis rotation of reposable section 14 (FIG. 4), more specifically, a selected end effector 28 disposed at the distal tip of bending section 24 as indicated by motion arrow 29. This is accomplished by the rotation of pushrod 36 disposed in hollow sheath 22 as controlled or moved by rotary thumb actuator 32 mounted on handpiece 12.

Pushrod 36 is cylindrical with a non-round shaped tip that is pushed through the center of the teeth 38 that are mounted on lock assembly 40 disposed in handpiece 12. Pushrod 36 is aligned with the center of teeth 38 of the lock assembly and extends through the center of the assembly. Pushrod 36 continues further until it engages and is positioned inside rotary thumb actuator 32 where it mechanically mates against a non-round inside wall. Pushrod 36 does not bottom out against the proximal end of rotary thumb actuator 32. Instead, it is allowed clearance to slide back and forth axially inside rotary thumb actuator 32. The total linear distance in which pushrod 36 can slide is determined by the travel needs of bending section 24 as it bends from a straight line to its maximum deflected position. Also compensated for is the travel distance of end effecter 28 as it opens and closes as required. Both events are able to occur simultaneously. Rotary thumb actuator 32 is fixed to the four quadrant control 30. Rotary thumb actuator 32 rotates radially about the center axis but is fixed in position axially to four quadrant controller 30 and does not move forward or backward.

Figures 6, 9:
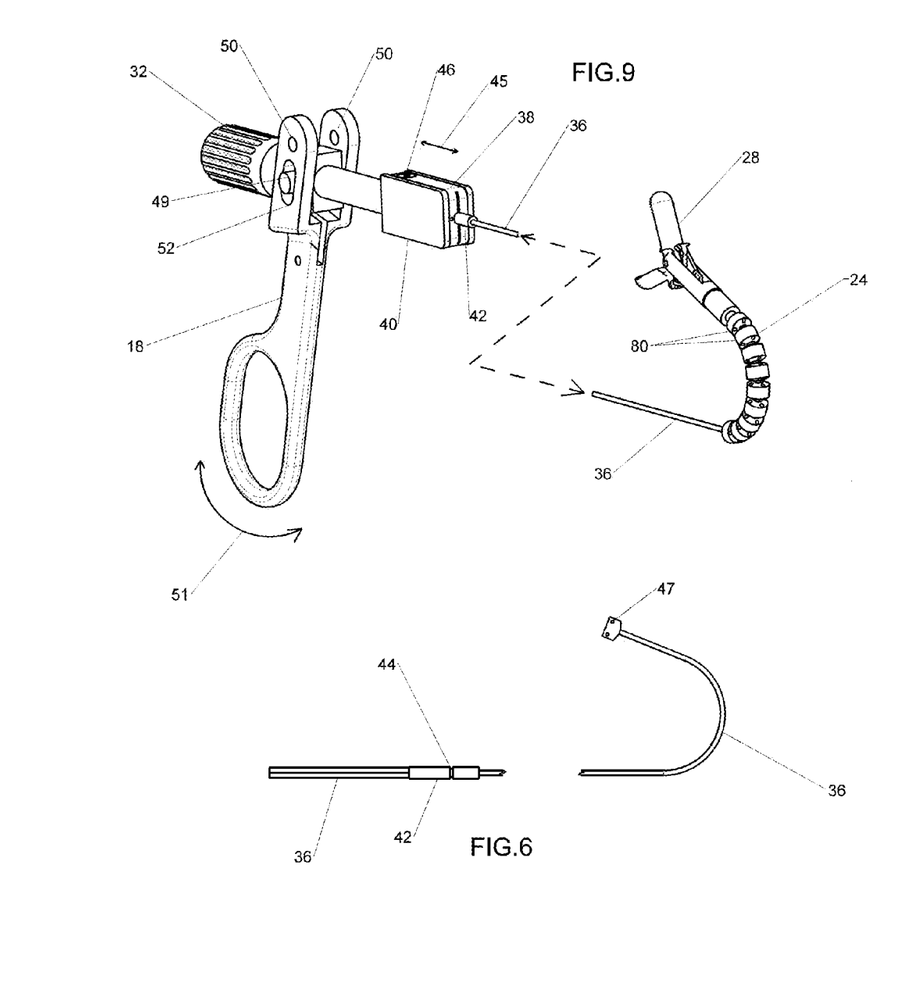
FIG. 6 is a partial side view of a component of FIG. 1.
FIG. 9 is a perspective view of the component of FIG. 5.
Figure 7:
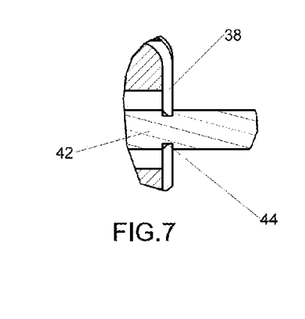
FIG. 7 is a partial cross-sectional view of the component of FIG. 6.
Figure 8:
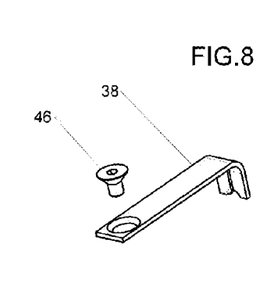
FIG. 8 is a perspective view of a component of FIG. 5.

As shown in FIGS. 6 and 7, the proximal end 42 of pushrod 36, which fits within handpiece 12 and is of a larger diameter and different shape than the much longer distal portion, has a cylindrical notch 44. The backside of notch 44 engages the front side of teeth 38 mounted on lock assembly 40 by locator screws 46 (FIGS. 8 and 9). Teeth 38 provide a clamping force against pushrod proximal end 42 within notch 44 thereby keeping the entire pushrod fixed within lock assembly 40. Therefore, when rotary thumb actuator 32 is turned in either radial direction, end effecter 28, mounted on pushrod endplate 47, will turn in compliance with the rotation of the actuator. Rotary thumb actuator 32 thereby drives the rotation of the end effecter of pushrod 36.

As described above, flexible metal teeth 38, as shown in perspective in FIG. 8, are secured to lock assembly 40 with two locator screws 46, one for each tooth. Lock assembly 40 travels forward and in reverse and is controlled by the trigger handle 18 closing against finger grip 20. The front side of each tooth pushes against the backside of the cylindrical notch and drives the pushrod forward. End effecter 28 then closes. When the trigger handle 18 is pulled in the opposite direction away from the finger grip 20, lock assembly 40 travels in reverse, the opposite side of notch 44 is pushed, and end effecter 28 opens.

As shown in FIG. 7, the backsides of the teeth are also beveled to allow the disengagement of the pushrod when handpiece 12 and reposable section 14 are separated. The cylindrical nature of notch 44 allows pushrod 36 to be rotated radially while simultaneously fixing it into position axially.

As further illustrated by FIG. 9, lock assembly 40 is shuttled forward and in reverse, proximally and distally, as indicated by arrow 45, by the action (arrow 51) of trigger handle 18. Lock assembly 40 also travels axially through the distal portion of rotary knob 32, using the rotary actuator as a guide. Lock assembly 40 is also connected to trigger handle 18 by means of two outboard pins 49 (one not shown) that may be a molded feature of lock assembly 40. Trigger handle 18 is further connected to handpiece 12 on swing pivots 50 (FIG. 9). The swing pivot may be a molded feature of the handpiece 12. Engagement slots 52 in trigger handle 18 receive the outboard pins 49. When the trigger handle 18 is moved, outboard pins 49 impart the driving force to move lock assembly 40. Engagement slots 52 allow the required clearance necessary for the arc travel of trigger handle 18 without binding against lock assembly 40. The user places their thumb into the ring of trigger handle 18 and their fingers into the ring of finger grip 20. Closing the hand provides the force to shuttle the lock assembly 40 back and forth, thereby manipulating end effecter 28.

The positioning of an end effecter at a desired orientation at a surgical site within the body can be provided by articulation and in this instrument is achieved by the use of four cables extending from the handpiece to the distal end of the bending portion where they are attached in an orthogonal array such that by withdrawing one cable toward the proximal end and simultaneously releasing its corresponding opposite cable disposed directly across from the cable being withdrawn, the end effecter will move up or down, left or right, and toward or away from the surgeon depending upon which cable pair is selected for manipulation. This may be carried out manually by, for example, thumbwheel devices or preferably as described below by a motorized system using driving motors, appropriate gear systems, and a hand operated control to select the desired angle and amount of articulation.

Figure 10:
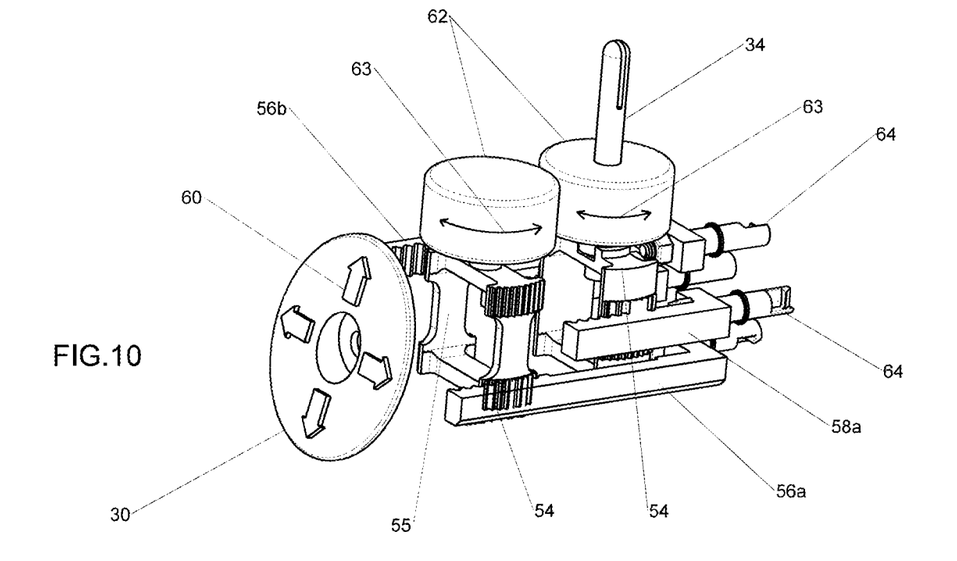
FIG. 10 is a perspective detailed view of an internal assembly of a component of FIG. 3.

Referring to FIG. 10, there are two sets of two rotatable motion motor gears 54 mounted on motor gear frame 55 which drive two sets of associated linear motion gear rack pairs 56*a* and 56*b*, and 58*a* and 58*b*, all of which are mounted inside handpiece 12. When used in combination they cause articulation up and down and also articulation left and right. The resultant motion of articulation is not limited to up, down, left or right. The hand operated control, as indicated by four quadrant control directional arrows 60 (FIG. 10), allows for any angle between these positions. In this instrument the two motors convert rotary motion to linear motion using the gear drive that causes the end effecters to travel in a circular trajectory.

Two reversible motors 62 (FIG. 10), one each for manipulating each pair of opposing articulating cables, are wired to four quadrant control 30 and installed in handpiece 12. Four quadrant control 30 is mounted onto the back of handpiece 12 and is marked with the directional arrows 60 that indicate direction of articulation. Each opposing arrow operates a switch that in turn activates one or the other of the motors in the appropriate direction as indicated by arrows 63. Four quadrant control 30 is also wired to a remote motor power supply (not shown) that may be controlled by foot pedals set on the floor of an operating room and within easy reach of the surgeon.

When pressure is applied to any arrow 60 on four quadrant control 30, the corresponding motor gear turns in the corresponding direction. The appropriate gear rack will move either forward or in reverse, arrows 65 (FIG. 13), depending upon which arrow is pressed. As a gear rack moves forward, its opposite corresponding gear rack moves in the opposite direction, the motor gear teeth meshing with the gear rack teeth. When not energized, the motors are used as a positive locking mechanism for the entire assembly, that is, at rest, the gear racks cannot move. In this embodiment, two motors drive four cables. An alternative embodiment is four motors, software controlled, driving one cable each.

Figure 13:
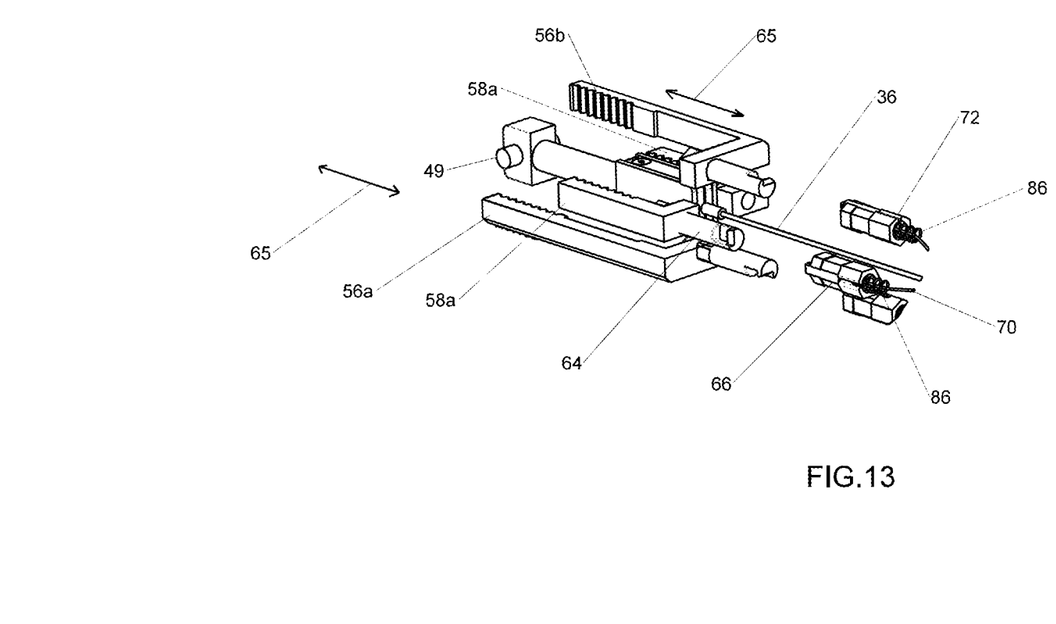
FIG. 13 is a perspective view of a portion of the assembly of FIG. 10.
Figure 14:
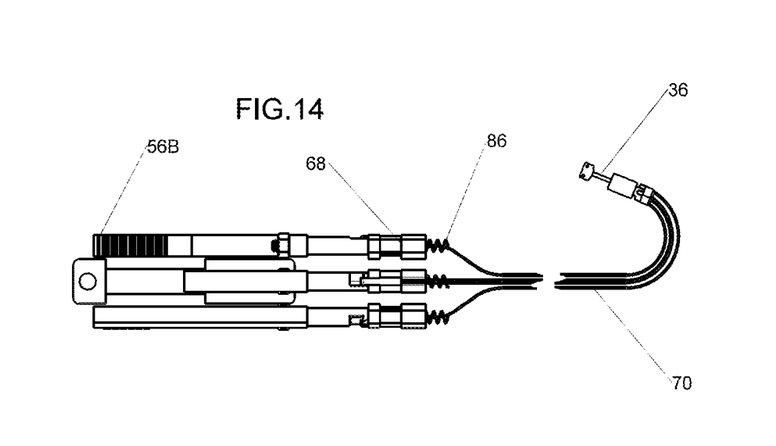
FIG. 14 is a side view of a portion of the assembly of FIG. 10.

As shown in FIGS. 13 and 14, the distal ends of the gear racks are connected to connector pins 64. Connector pins 64 are shaped in a specific way that allows them to easily release away from opposing mating connector clips 66, FIG. 12, which are located in reposable section 14 shown in FIG. 4.

Figure 11:
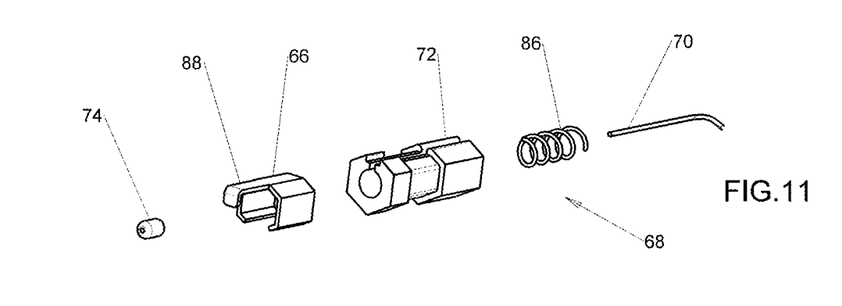
FIG. 11 is an exploded perspective view of a component of FIG. 4.
Figure 12:
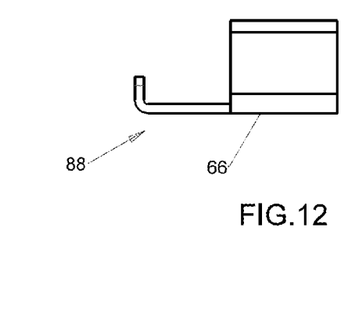
FIG. 12 is a side view of a component of FIG. 11.
Figure 15:
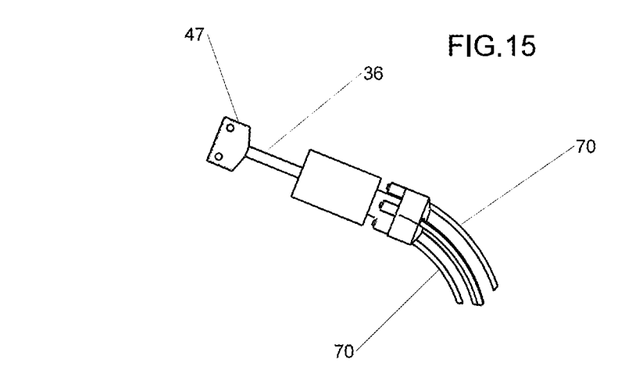
FIG. 15 is a side view of a portion of the assembly of FIG. 14.
Figure 16:
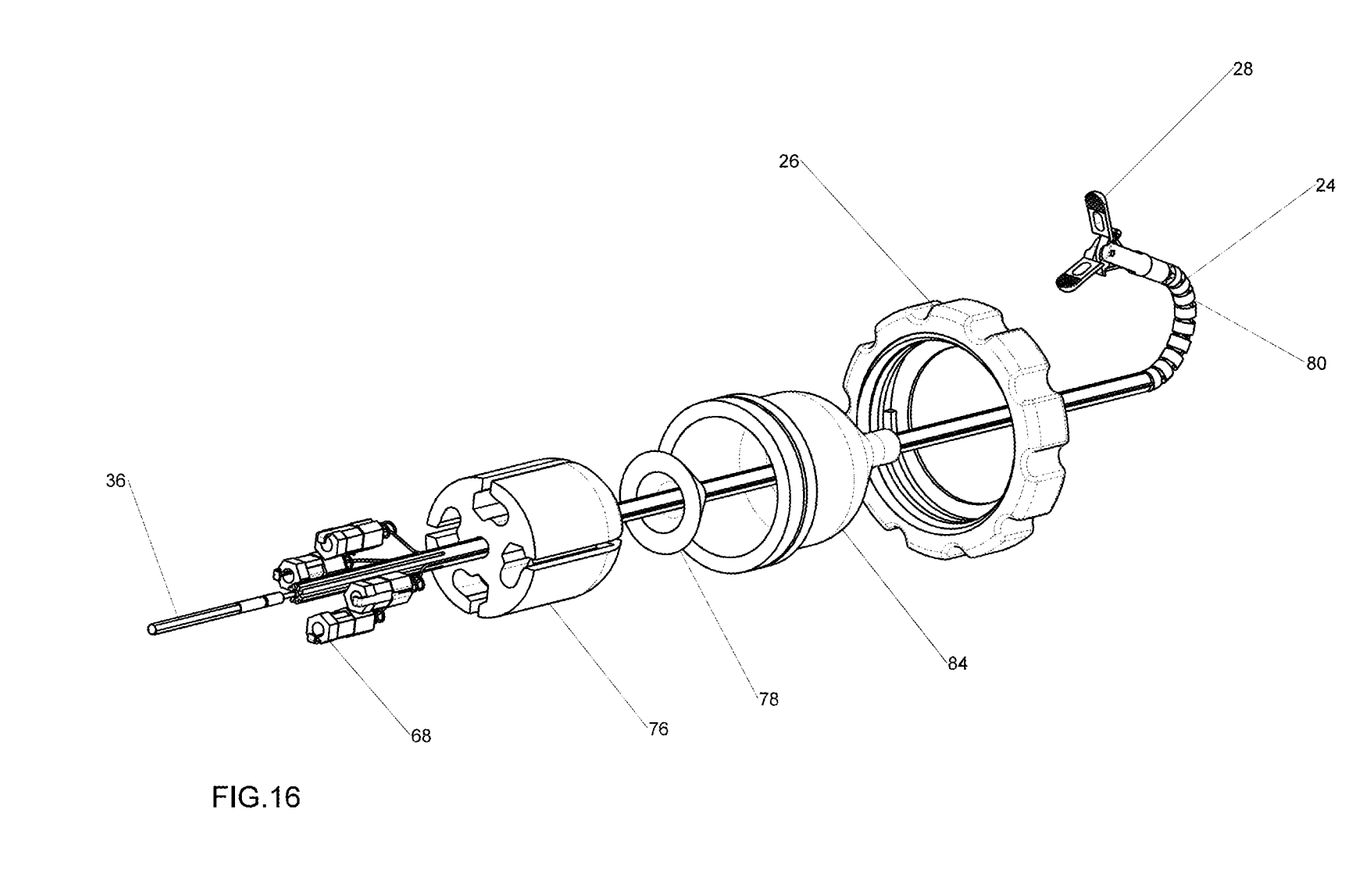
FIG. 16 is a detailed perspective view of the component of FIG. 4.

Reposable section 14 connects to handpiece 12 to form the complete multiscopic surgical instrument. Reposable section 14 includes two sets of opposing cable assemblies and a selected end effecter of choice. Each cable assembly 68, with its component parts shown in FIG. 11, is further comprised of a cable 70 assembled to a connector housing 72 by means of a crimp connector 74 which in turn is snapped onto a connector clip 66. Cable guides 76 and 78 are shown in FIG. 16. The two cable sets are paired and are arranged for articulation of bending section 24 up and down and left and right. When a directional arrow 60 on four quadrant control 30 is pushed, thereby activating one of the appropriate motors 62, a gear rack pulls on its mating cable assembly while the opposite mating cable assembly is released by the opposite gear rack to travel in the opposite direction. FIG. 15 shows the attachment of opposing cables 70 to the distal end of bending section 24.

Figure 17:
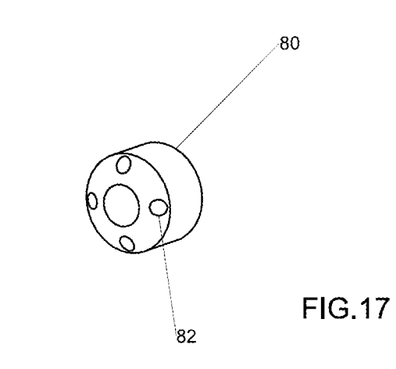
FIG. 17 is a perspective view of a component of FIG. 9.
Figure 18:
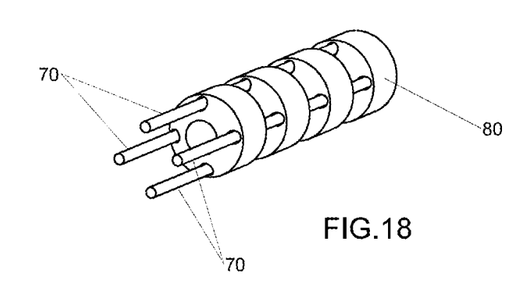
FIG. 18 is an additional perspective view of a portion of FIG. 9.

Reposable section 14 may be composed of a linked together plurality of individual segments 80 (FIG. 16) each having two sets of orthogonal ports 82 serving as cable guides, a section of which is shown in FIGS. 17 and 18.

When connecting articulator section 14 to handpiece 12, the first contact is made by pushrod 36 which extends beyond the base of the reposable section 14 bottom by a length that is long enough to snap the pushrod notch 44 against teeth 38 of the lock assembly 40. As pushrod 36 enters the center of the lock assembly 40 teeth set, the four connector clips 66 simultaneously snap and lock onto the four connector pins 64. Pushrod 36 is longer than the extension of the connector clips 66 and enters handpiece 12 and the lock assembly before connector clips 66 are snapped into the four connector pins 64 (FIG. 13).

Reposable section 14 includes a trocar adapter 84 (FIG. 16) which engages and locks against handpiece 12. Compression springs 86 apply pressure against connector pins 64. The spring force ensures simultaneous constant pressure against all four of the connector pins allowing for simultaneous connection of the four connector pins to the four connector clips and additionally provides for slack removal. Reposable section 14 is finally securely joined to handpiece 12 by nut 26.

To separate reposable section 14 and handpiece 12, nut 26 is unscrewed. As the nut is being unscrewed, the back wall of the nut presses against the back wall of trocar adapter 84 causing the two components, reposable section 14 and handpiece 12, to separate. The connector clips 66 (FIG. 11) in the reposable section are pulled at the same time but are stopped by the length of the cable. The continued travel of reposable section 14 causes the right angle clip extension 88 on the connector clip 66 to go past its yield point and straighten out. In this straightened condition, the four connector clips 66 cannot be used a second time and thereby rendering reposable section 14 unusable for continued use. In a further related embodiment, nut 26 is rotatably mounted on trocar adapter 84, so that unscrewing the nut from the handpiece 12 simultaneously causes the trocar adapter 84 to be removed from the handpiece 12.

The embodiments of the invention described above are intended to be merely exemplary; numerous variations and modifications will be apparent to those skilled in the art. All such variations and modifications are intended to be within the scope of the present invention as defined in the appended claims.

What is claimed is:

1. An articulating surgical instrument for endoscopic surgical procedures, the instrument comprising:
   a case having a handpiece portion, the handpiece portion having handle and a trigger;
   an assembly including:
   a sheath, having a set of passageways therein, with a proximal end coupled to the case, wherein the sheath defines a longitudinal axis and the handle is mounted in fixed relation to the longitudinal axis;
   a flexible bending section having a proximal end coupled to a distal end of the sheath; and
   an end effector mounted to a distal end of the bending section;
   wherein the case is configured to be removably attachable, as an integral unit without need for disassembly thereof, to the assembly;
   a set of cables, coupled to the flexible bending section and disposed in the sheath, that control position of the distal end of the bending section;
   a set of at least two motors, disposed in the case, coupled to the set of cables, so as to control position of the distal end of the bending section;
   a user control module, coupled to the set of motors, configured to control position of the bending section and therefore of the end effector; and
   a flexible pushrod, disposed within the sheath and within the bending section, configured for both (i) axial motion relative to the sheath and the bending section and (ii) rotational motion within the sheath and the bending section, the pushrod having a proximal end coupled to the trigger and a distal end coupled to the end effector;
   wherein rotational motion of the pushrod effectuates rotation of the end effector and axial motion of the pushrod, controllable by the trigger, causes the end effector to move between an open position and a closed position.

2. An instrument according to claim 1, wherein each of the cables is removably coupled to a corresponding connector pin in the case, and the connector pins in the case are coupled to the set of motors.

3. An instrument according to claim 2, wherein (a) each of the cables is removably coupled via a connector clip to a corresponding connector pin in the case; (b) each connector clip is configured to be deformed upon removal of the assembly from the case; (c) deformation of such connector clip prevents its operable recoupling to the connector pin, so that the assembly cannot be reattached to the case in a manner enabling reuse of the assembly after it has been removed from the case.

4. An instrument according to claim 1, wherein the handle has a gripping axis around which fingers of a user can be placed and the gripping axis is transverse to the longitudinal axis.

5. An articulating surgical instrument for endoscopic surgical procedures, the instrument comprising:
   a case having a handpiece portion having a handle and a trigger;
   a sheath, having a set of passageways therein, with a proximal end coupled to the case, wherein the sheath defines a longitudinal axis and the handle is mounted in fixed relation to the longitudinal axis;
   a flexible bending section having a proximal end coupled to a distal end of the sheath;
   an end effector rotatably mounted to a distal end of the bending section;
   a set of cables, coupled to the flexible bending section and disposed in the sheath, that control position of the distal end of the bending section;
   a user control module, coupled to the set of cables, configured to control position of the bending section and therefore of the end effector; and
   a flexible pushrod disposed within the sheath and flexible within the bending section, configured for both (i) axial motion relative to the sheath and the bending section and (ii) rotational motion within the sheath and the bending section, the pushrod having a proximal end coupled to the trigger handle and a distal end coupled to the end effector,
   wherein:
   (a) the case is configured to be removably attachable, as an integral unit without need for disassembly thereof, to an assembly that includes the sheath, the bending section, and the end effector and (b) rotational motion of the pushrod effectuates rotation of the end effector and axial motion of the pushrod, controllable by the trigger, causes the end effector to move between an open position and a closed position.

6. An instrument according to claim 5, wherein each of the cables is removably coupled to a corresponding connector pin in the case, and the connector pins in the case are coupled to user control module.

7. An instrument according to claim 6, wherein (a) each of the cables is removably coupled via a connector clip to a corresponding connector pin in the case; (b) each connector clip is configured to be deformed upon removal of the assembly from the case; (c) deformation of such connector clip prevents its operable recoupling to the connector pin, so that the assembly cannot be reattached to the case in a manner enabling reuse of the assembly after it has been removed from the case.

8. An instrument according to claim 5, wherein the handle has a gripping axis around which fingers of a user can be placed and the gripping axis is transverse to the longitudinal axis.

* * * * *

UNITED STATES PATENT AND TRADEMARK OFFICE
CERTIFICATE OF CORRECTION

| | | |
|---|---|---|
| PATENT NO. | : 9,675,329 B2 | Page 1 of 1 |
| APPLICATION NO. | : 14/057714 | |
| DATED | : June 13, 2017 | |
| INVENTOR(S) | : Gerry Berkelaar | |

It is certified that error appears in the above-identified patent and that said Letters Patent is hereby corrected as shown below:

In the Claims

In Column 7, Line 39:
Replace "having handle"
With "having a handle"

Signed and Sealed this
Third Day of October, 2017

Joseph Matal
*Performing the Functions and Duties of the*
*Under Secretary of Commerce for Intellectual Property and*
*Director of the United States Patent and Trademark Office*